United States Patent
Massen et al.

[11] Patent Number: 5,604,817
[45] Date of Patent: Feb. 18, 1997

[54] TOOTH MEASUREMENT WITHOUT CALBRATION BODIES

[75] Inventors: Robert Massen, Wangen/Öhningen; Christian Konz, Radolfzell; Joachim Gässler, Geisingen; Harald Richter, Constance, all of Germany

[73] Assignee: Kaltenbach & Voigt GmbH & Co., Bismarckring, Germany

[21] Appl. No.: 108,390

[22] Filed: Aug. 18, 1993

[30] Foreign Application Priority Data

Sep. 3, 1992 [DE] Germany .................... 42 29 466.5

[51] Int. Cl.$^6$ ........................................... G06K 9/00
[52] U.S. Cl. ................. 382/120; 348/66; 356/376; 364/560; 433/215; 382/154; 382/284
[58] Field of Search ................. 382/6, 34; 348/66; 364/560; 356/376; 128/776, 6; 433/29, 215; 33/513, 514

[56] References Cited

U.S. PATENT DOCUMENTS

| | | |
|---|---|---|
| 4,575,805 | 3/1986 | Moermann et al. .................... 348/66 |
| 5,339,154 | 8/1994 | Gassler et al. .................... 356/376 |
| 5,369,490 | 11/1994 | Kawai et al. .................... 356/376 |
| 5,372,502 | 12/1994 | Massen et al. .................... 433/215 |

FOREIGN PATENT DOCUMENTS

WO90/05483  5/1990  WIPO.

*Primary Examiner*—Leo H. Boudreau
*Attorney, Agent, or Firm*—Scully, Scott, Murphy and Presser

[57] ABSTRACT

A method for the optical three dimensional measurement of a tooth without calibration bodies. An optical projection system projects a pattern onto a tooth, and an optical imaging system images the pattern projected thereon, from a first position in space and subsequently from a second position in space, with the images from the two positions in space having a common imaged area of the tooth. The image patterns are evaluated to calculate three dimensional coordinate data of the tooth surface relative to the respective imaging position for each image and also for the two images combined, to produce a single three dimensional tooth surface data record. In this method, points and/or surfaces are selected from the common imaged area with the aid of properties of the tooth surface contour which are invariant under displacement and rotation, so that they can be clearly correlated with each other. The change in position between the first and second positions in space is determined with the aid of the selected points and/or surfaces and their relative coordinate data.

15 Claims, 4 Drawing Sheets

TOOTH MEASUREMENT WITHOUT CALBRATION BODIES

TECHNICAL FIELD OF THE INVENTION

The present invention relates to a method for 3D-measurement of a tooth without the use of calibration bodies.

BACKGROUND OF THE INVENTION AND PRIOR ART

Two different approaches are known from the prior art which attempt to solve the problems of coordinating several images from different imaging positions.

Generally a tooth is optically imaged from different imaging positions, as it is only possible to image one certain area of the tooth on account of the limited imaging area of an imaging system. The obtained images, which jointly cover the entire tooth, are brought together on completion of the imaging to give a single 3D-data record which clearly describes the contour of the tooth. The prior art presents various methods for bringing the images together and calculating the 3D-data record, which methods will be discussed briefly in the following.

Basically, the coordinate data of the imaged tooth contour determined in one image and relating in each case to a system of coordinates which is dependent upon the position of the imaging system must be transformed into a common system of reference coordinates. Such a transformation is rendered possible, on the one hand, in that before the imaging small calibration bodies are arranged around the tooth. The individual imaged areas of the tooth must be selected so that at least two identical calibration bodies are visible on adjacent images. As the external dimensions of the calibration bodies and their exact position in space are measured with great accuracy at the beginning of the imaging sequence; adjacent images and the determined relative coordinate data of the tooth contour can thus be correlated with each other in a defined manner in each case by means of a transformation matrix which indicates the change in location (WO90/05483).

The disadvantage of this method is that the use of calibration bodies is unpleasant for the patient and proves to be a complicated procedure for the dentist. Moreover, these calibration bodies, in so far as they are fitted on the tooth, cover a portion of the tooth which is thus not visible in the image. For this reason, the selected calibration bodies ought to be as small as possible, in which case, however, exact measurement is impaired, leading to inaccurately calculated coordinate data.

A further method for optical 3D-measurement of teeth or groups of teeth in the oral cavity of a patient consists of determining absolute coordinate data of the tooth contour with the aid of a rigid multiple arrangement of projection and imaging optical systems in a mouth probe head. The use of calibration bodies can be foregone, as the individual positions in space relative to a common system of coordinates are known on account of the rigid arrangement of the projection and imaging systems. The disadvantage of this method, however, lies in the fact that a large number of imaging and projection channels are required, which channels have to be guided via endoscopic systems or light guides from the oral cavity to the relevant image sensors and projection units. As the portion of the imaging and projection apparatus introduced into the oral cavity is to be separable for the purposes of disinfection and cleaning, the large number of optical endoscopic channels signifies a considerable expenditure on account of the necessary high mechanical precision of the coupling mechanism.

OBJECT OF THE INVENTION

The object of the present invention consists in reducing the number of the optical imaging/projection channels, whereby a great technical simplification and considerable minimization of costs are achieved and the use of calibration bodies can be dispensed with.

SUMMARY OF THE INVENTION

According to the present invention there is provided a method for optical 3D-measurement of teeth without calibration bodies, with at least one optical projection system being provided for the projection of patterns onto a tooth and an optical imaging system being provided for imaging the patterns projected onto the tooth, comprising the steps:

projection of a pattern onto the tooth and imaging the pattern reflected by the tooth, from a first and subsequently from a second position in space, with the images from the two positions in space having common imaged areas of the tooth; and evaluation of the imaged patterns, with 3D-coordinate data of the tooth surface relative to the respective imaging position being calculated for each image and the two images being combined to give a single 3D tooth-surface data record, wherein points and/or surfaces are selected from the common imaged areas of the two images, their selection being effected with the aid of properties of the tooth surface contour which are invariant under displacement and rotation, so that they can be clearly correlated with each other, and wherein the change in location between the first and the second position in space is determined with the aid of the selected points and/or surfaces and their relative coordinate data.

Embodiments of the invention can include further advantageous developments.

BRIEF DESCRIPTION OF THE DRAWINGS

The objects, features and advantages of the present invention are evident from the description and the accompanying drawings, in which.

DETAILED DESCRIPTION OF PREFERRED EMBODIMENTS ACCORDING TO THE INVENTION

Figure 1:
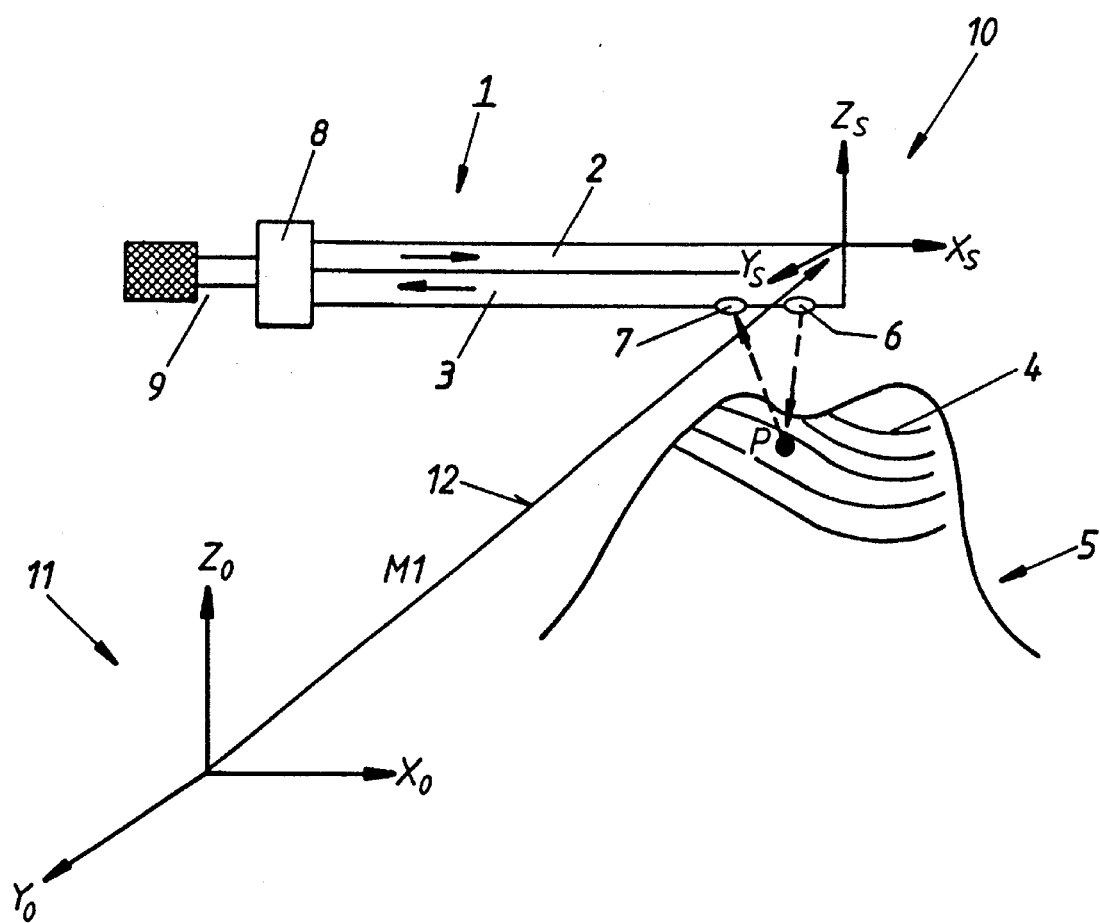
FIG. 1 shows, by way of example, an imaging and projection system.

In the case of optical 3D-measurement of teeth or groups of teeth with the known methods of phase-shift techniques, Moiré-techniques and similar interferometric 3D-measuring techniques, in each case it is only possible to measure a partial view of an entire body. These measuring methods supply XYZ-space coordinates only of that part of the surface of the body to be measured which is covered both by the beam path of the strip projection optical system and also by the beam path of the imaging optical system. It is therefore always necessary to bring such an optical measuring probe into numerous different imaging positions relative to the body in order to cover the whole surface of a body successively. The measuring probe 1 itself consists of two endoscopic systems or light guides 2, 3, with a pattern 4, which is to be projected onto the tooth 5, being directed to a lens system 6 by way of the endoscopic system 2 and the projected image being directed by way of a lens system 7 and the return endoscopic system 3 to a CCD-sensor (which is not represented in the Figure). The endoscopic systems 2, 3 are coupled to the respective projectors or CCD-sensors by means of a coupling point 8. Furthermore, a guiding. mechanism 9 is provided at the coupling point, making it possible for the operator to move the measuring probe 1.

With the aid of the imaged pattern 4, a computer determines a 3D-coordinate data record which specifies the tooth contour which lies in the imaging area. In this connection, it is of course assumed that the internal parameters of the measuring probe, such as, for example, the focal distance of the lens system, are known in full. The calculated coordinate data relates to a coordinate system 10 relative to the mouth probe 1, which system is displaced by a vector 12 ($M_1$) with respect to an original system of coordinates 11.

Figure 2:
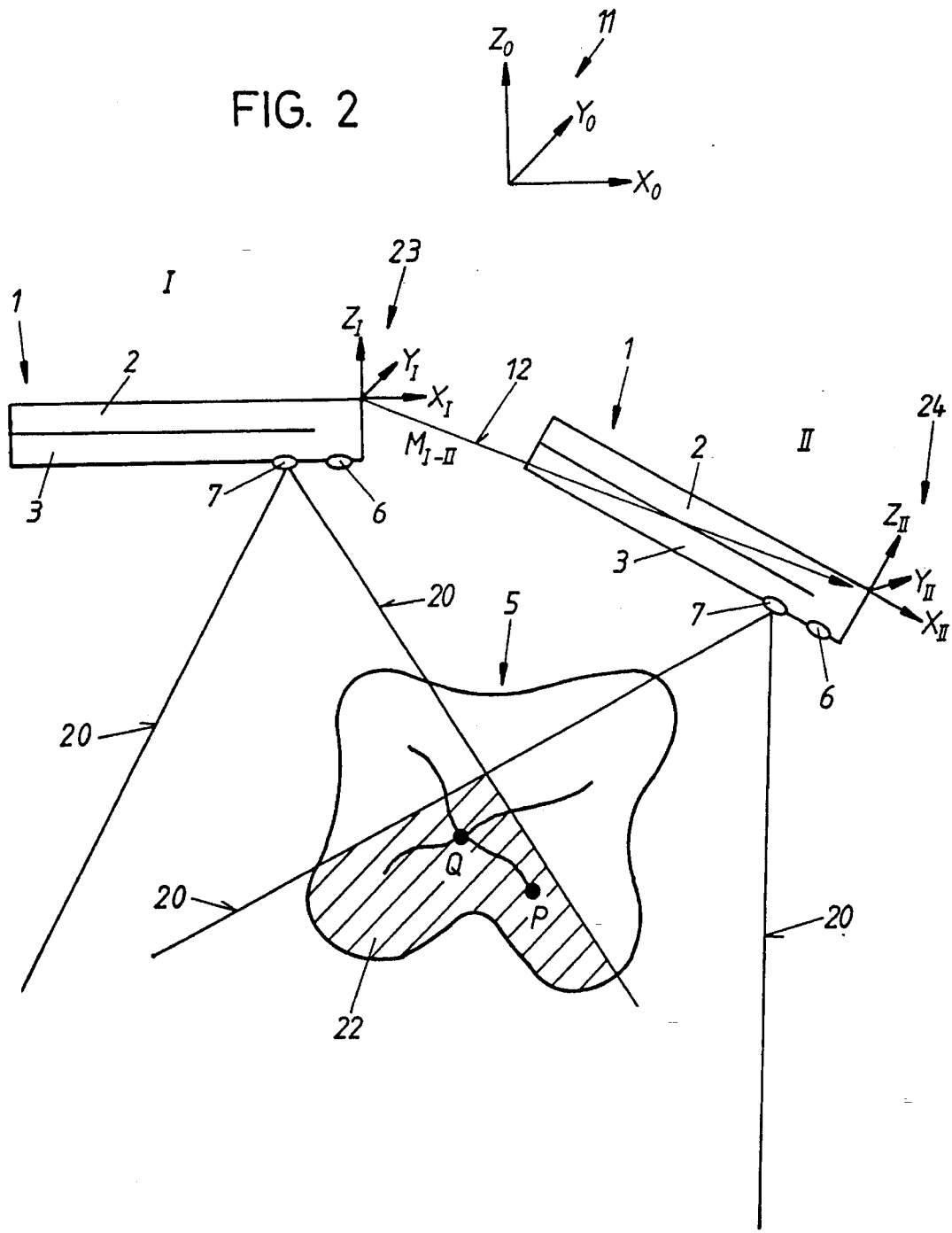
FIG. 2 shows the geometrical relationships for two successive images from different positions in space.

FIG. 2 illustrates clearly that a measuring probe 1 can only image one partial area of the tooth, defined by the two boundary lines 20. As previously mentioned, it is for this reason that several images from different positions in space are produced. In FIG. 2, for this reason the measuring probe 1 has been guided out of position I into a position II. Here as well, the imaging area of the measuring probe 1 is marked by boundary lines 20. In this connection, it is to be noted that the two images overlap to a considerable extent, this being indicated by the hatched area 22. The calculated coordinate data of the imaged areas of the tooth 5 relates in each case to the measuring probe coordinate system 23 or 24 respectively.

A relationship between the two coordinate systems 23, 24 mentioned can be established with the aid of a transformation matrix T1 which contains the unknown degrees of freedom of translation and rotation:

$$P_2 = P_1 * T1$$

In this connection $P_1$ is the vectorial description of the position of the point P in the internal measuring coordinate system 23 and $P_2$ is the vectorial description of the same point of the tooth surface in the internal measuring coordinate system 24.

The problems in determining a single coordinate data record now lie in finding such transformation matrixes between two imaging positions in order thus to be able to relate all coordinate data to a common coordinate system.

Mathematically, the above equation with its six unknown parameters, namely three translatory and three rotatory degrees of freedom, can be solved by the selection of six points from the respective, overlapping area of an image. In this connection, however, it is assumed that the respective six points on each image can be clearly correlated to each other.

Figure 3A:
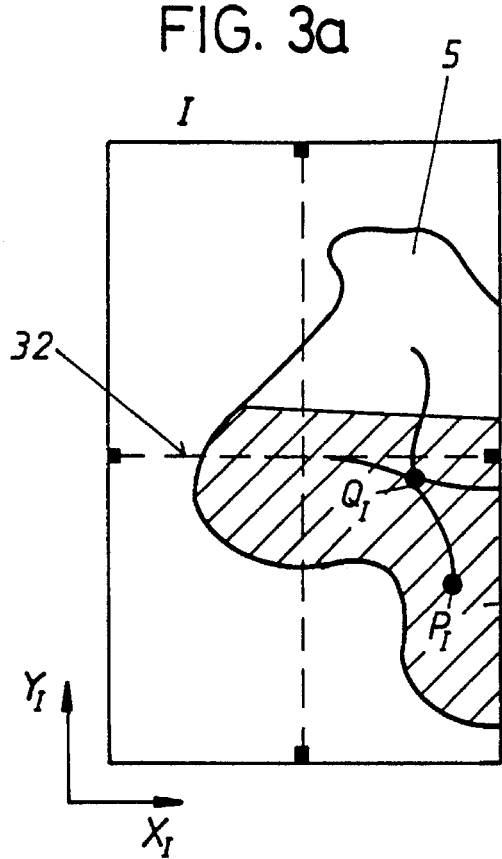
FIGS. 3a and 3b illustrate respectively, by way of example, the respective images from the two positions in space.
Figure 3B:
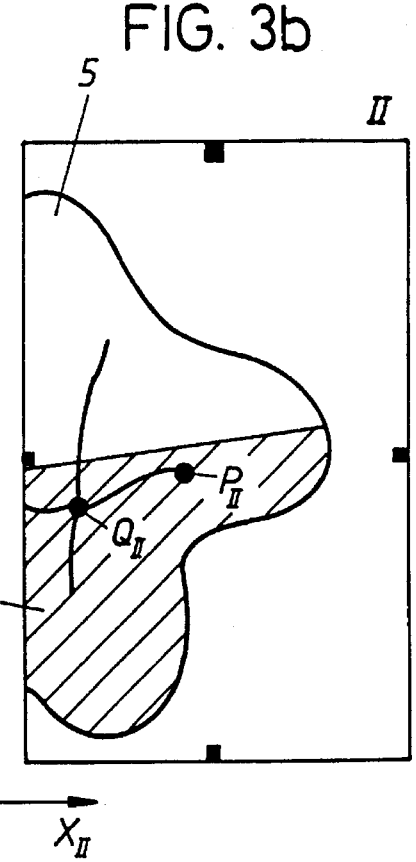

This will be explained again with the aid of FIGS. 3a and 3b. FIG. 3a shows, by way of example, a partial image of the tooth 5 from a first position in space I and FIG. 3b shows a partial image of the tooth 5 from a second imaging position II. Both images, as already shown in FIG. 2, cover a common area 22. In this area, two points P and Q are marked for the illustration of the rest of the procedure. The way in which such points are selected is explained in detail in another passage.

The coordinate data of the point P is determined in the first image as $P_1$ and in the second image as $P_2$, in each case relative to the internal measuring probe coordinate system 23 or 24 respectively. The same holds true as well in a corresponding manner for the point Q which has been drawn in. It becomes clear from the two FIGS. 3a and 3b that the points P and Q have different coordinate data in the respective imaging positions, with it being possible to convert the point $P_1$ into point $P_2$ with the aid of the above-mentioned transformation matrix T1. An equation system for determining this transformation matrix T1 is clearly determined by selection of six points, because of the six unknown parameters.

The selection of points, which must at any rate lie in the overlapping area 22, can take place in two ways. On the one hand, there is the possibility for the dentist to select certain points on the tooth which he recognizes in both images, for example on the screen. The selection itself is made easy for him by modern video technology. The measuring probe 1 supplies a real time video image for this, which image can be observed constantly by the dentist. In addition, the dentist is able to store each real time video image which appears on the monitor and when a second imaging position is approached, furthermore, to fade this in on the screen. This represents a considerable improvement in ease for the dentist. On the one hand, when a new imaging position is approached, by comparing the real time video image and the stored image he can recognize right away to what extent the two imaged areas overlap. On the other hand, this video method assists the dentist when selecting the points which must be clearly recognizable on both images and capable of correlation.

When the dentist has selected certain points, the system can, as already described, convert the coordinate data of the second image by means of transformation of coordinates into the internal coordinate system of the first image.

According to the invention, the selection of the points can, however, also be effected automatically. For this, with each image and for a selection of points the system must calculate the properties thereof which are invariant under translation and rotation. Such a property would, for example, be the surface curvature at one point, the curvature being described as a value which specifies the minimum radius of a sphere laid into this point and adjacent points. The calculation of a transformation matrix is effected as already described, with the aid of the selected points which the system can correlate with each other.

Figure 4:
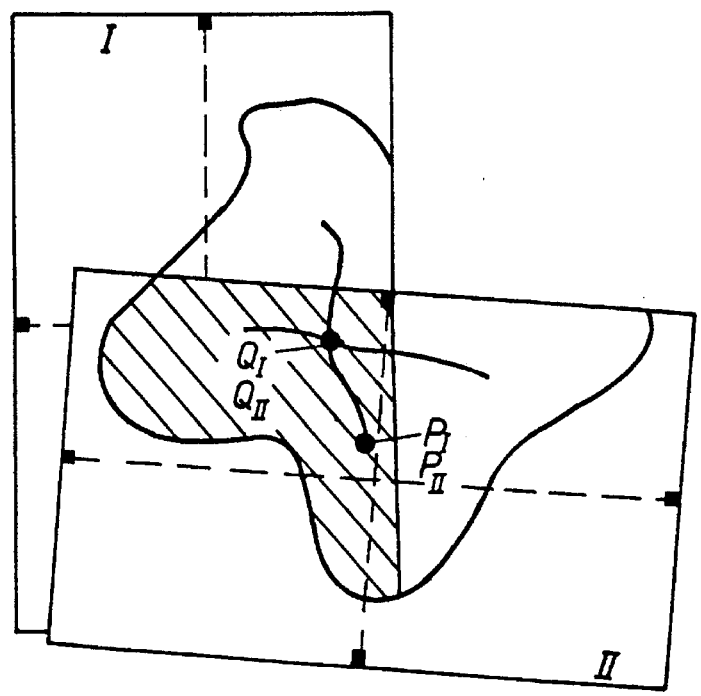
FIG. 4 shows the fitting of the second image to the first image.

As it is difficult for the system to identify clearly correlatable points in pairs of images and errors thus result during the calculation of the transformation matrix, this method is only used for a rough estimate of the change in position in space. The actual determination of the transformation matrix is effected with the aid of a best-fit matching. Such a best-fit method is known to the specialist and is not therefore described in greater detail in the following. Essentially this method consists in fitting the image from the second position to the image of the first position in such a way that a minimum square error results between corresponding points of the two images, as illustrated in FIG. 4.

Figuratively speaking, with the best-fit method all possible combinations of the change in location between position I and position II are tested one after the other. In order to limit this infinitely large range of possible solutions, the coordinate transformation matrix search range is limited, and the method just mentioned for the rough estimate of the transformation matrix is first used. Other methods for systematically searching according to the rules of the best-fit are known from the literature. Numerous variants for reducing the search effort, such as, for example, linear dynamic programming, relaxation methods etc., are known to the specialist and shall not be repeated here.

The cross-shaped auxiliary marking 32 drawn in FIG. 3a is to provide the dentist with assistance when positioning the measuring probe. By observing the video image he can recognize whether, for example, the selected distance between measuring probe and tooth is correct and whether the tooth lies optimally in the imaging area. Basically, before each image is taken this marking is projected onto the tooth (not represented in FIG. 3b for the sake of clarity).

Figure 5:
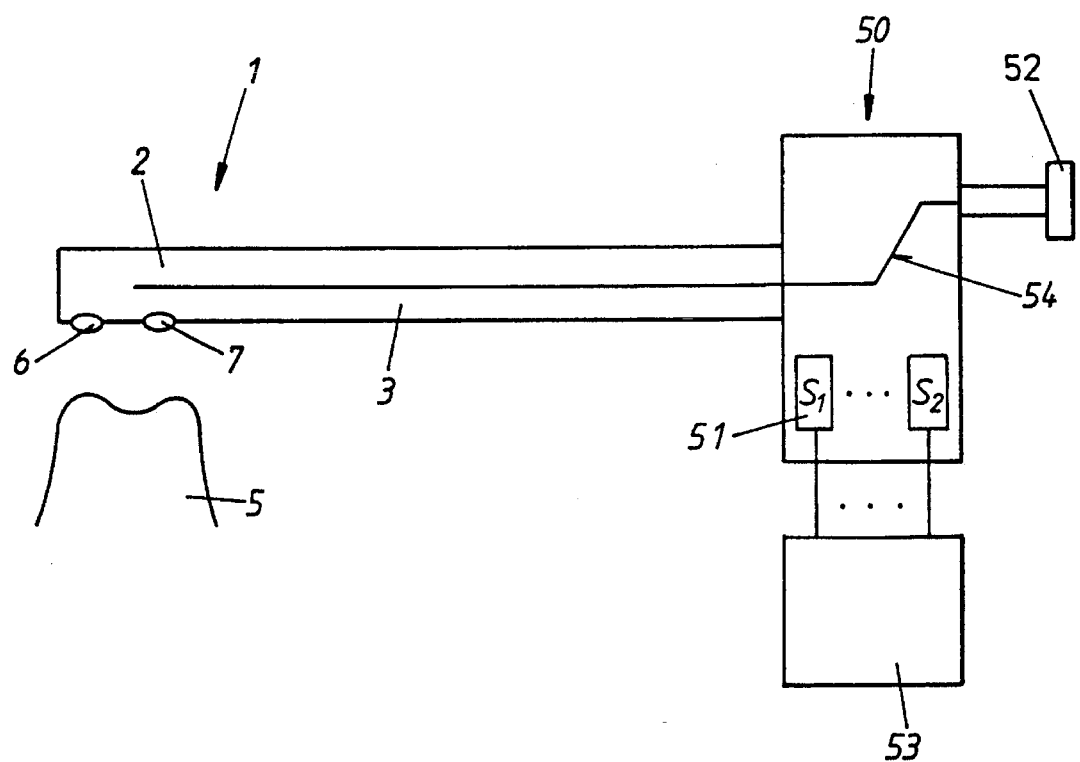
FIG. 5 diagrammatically shows an arrangement for the indirect movement of the imaging and projection system.

An understanding of a further possibility of reducing the search effort is to be given with the aid of FIG. 5. Here again, a measuring probe 1 with the endoscopic systems 2,3 and the lens systems 6, 7 is shown. In contrast to the arrangement shown in FIG. 1, the measuring probe is not held on a holder 9, by the operator. The movement of the measuring probe 1, according to the invention, is not effected directly, but by way of a manipulator 50 which retransmits the movement, carried out by the dentist, at a grip portion 52 indirectly by way of a guiding mechanism 54 to the measuring probe 1. In this connection, it is possible to provide sensors 51 in the manipulator, which sensors can transmit exact data on the change in location of the measuring probe 1 to an evaluating unit 53. Such sensors are, for example, linear or rotary transducers or position transmitters which operate without contact and which depend, for example, on the observation of an optical mark or an ultrasound source with optical or ultrasonic sensors. The evaluating unit 53 can calculate a rough estimate of the change in position with the aid of the positional data of the sensors 51, whereby the range of possible solutions of the best-fit method can be greatly limited.

Of course, the manual movement of the measuring probe 1 at the grip portion 52 can also be carried out by automatically operating drive elements, for example positioning motors.

What is claimed is:

1. Method for optical 3D-measurement of teeth without calibration bodies, with at least one optical projection system being provided for the projection of patterns onto a tooth and an optical imaging system being provided for imaging the patterns projected onto the tooth, comprising the steps:

projection of a pattern onto the tooth and imaging the pattern reflected by the tooth, from a first position in space and subsequently from a second position in space, changed to be different from the first position in spaced, with the images from the two positions in space having common imaged areas of the tooth; and evaluation of the imaged patterns, with 3D-coordinate data of the tooth surface relative to the respective imaging position being calculated for each image and the two images being combined to give a single 3D tooth-surface data record, wherein points and/or surfaces are selected from the common imaged areas of the two images, their selection being effected with the aid of properties of the tooth surface contour which are invariant under displacement and rotation, so that they can be clearly correlated with each other, and wherein the change in position between the first and the second positions in space is determined with the aid of the selected points and/or surfaces and their relative coordinate data.

2. Method according to claim 1, wherein the curvature of the surface is determined for each point of the image, which curvature is defined by the point itself and adjacent points.

3. Method according to claim 2, wherein the curvature of the surface is defined by the smallest possible radius of a sphere which can be laid into the point itself and the adjacent points.

4. Method according to claim 1, wherein at least six points are selected.

5. Method according to claim 1, wherein an equation system is set up with the aid of the calculated coordinate data relative to the respective imaging position of the selected points of the two images, with which six unknown parameters of a coordinate transformation matrix can be calculated, corresponding to six degrees of freedom of the difference in position between the first and second positions.

6. Method according to claim 1, wherein the second image is fitted to the first image with the aid of the selected points and thus the difference in position between the first and second positions is determined.

7. Method according to claim 6, wherein the fitting is effected in such a way that a square error which results between corresponding points of the two images during the determination of a coordinate transformation matrix becomes minimal.

8. Method according to claim 7, wherein the fitting is accelerated by limiting a search for the coordinate transformation matrix.

9. Method according to claim 1, wherein a change in position of the projection system and imaging system is roughly determined by means of sensors provided thereon outside the oral cavity.

10. Method according to claim 9, wherein the projection and imaging system is secured to a hand-operated manipulator which has the sensors.

11. Method according to claim 10, wherein the manipulator is motor driven into known positions in space.

12. Method according to claim 9, wherein the sensors are linear and rotary transducers for rotation and translation of all possible degrees of freedom.

13. Method according to claim 9, wherein the sensors are position transmitters which operate without contact.

14. Method according to claim 1, wherein the imaging system delivers a real time video image which can be seen on a connected monitor.

15. Method according to claim 14, wherein the real time video image from the first position in space is stored and faded in when approaching the second position so that both the real time video image and the stored video image can be seen on the monitor.

* * * * *